United States Patent
Lee et al.

(10) Patent No.: US 10,653,663 B2
(45) Date of Patent: May 19, 2020

(54) PHARMACEUTICAL COMPOSITION FOR ORAL ADMINISTRATION COMPRISING TAXANE

(71) Applicant: DAE HWA PHARMA. CO., LTD., Gangwon-do (KR)

(72) Inventors: In-Hyun Lee, Gwangju (KR); Min-Hee Son, Uiwang-si (KR); Yeong-Taek Park, Ansan-si (KR); Seul-Ae Lee, Seongnam-si (KR); Han-Koo Lee, Seoul (KR)

(73) Assignee: DAE HWA PHARMA. CO., LTD., Gangwon-do (KR)

( * ) Notice: Subject to any disclaimer, the term of this patent is extended or adjusted under 35 U.S.C. 154(b) by 65 days.

(21) Appl. No.: 15/523,021

(22) PCT Filed: Jul. 30, 2015

(86) PCT No.: PCT/KR2015/007987
§ 371 (c)(1),
(2) Date: Apr. 28, 2017

(87) PCT Pub. No.: WO2016/068457
PCT Pub. Date: May 6, 2016

(65) Prior Publication Data
US 2017/0312244 A1    Nov. 2, 2017

(30) Foreign Application Priority Data
Oct. 31, 2014 (KR) .................. 10-2014-0150173

(51) Int. Cl.
| | | |
|---|---|---|
| *A61K 31/337* | (2006.01) | |
| *A61K 47/26* | (2006.01) | |
| *A61K 47/14* | (2017.01) | |
| *A61K 9/48* | (2006.01) | |
| *A61K 9/08* | (2006.01) | |
| *A61K 47/44* | (2017.01) | |
| *A61K 9/00* | (2006.01) | |

(Continued)

(52) U.S. Cl.
CPC .......... *A61K 31/337* (2013.01); *A61K 9/0053* (2013.01); *A61K 9/08* (2013.01);
(Continued)

(58) Field of Classification Search
None
See application file for complete search history.

(56) References Cited

U.S. PATENT DOCUMENTS

| | | | |
|---|---|---|---|
| 8,075,917 B2 | 12/2011 | Chung et al. | |
| 2002/0192280 A1* | 12/2002 | Hunter | A61K 9/0014 424/465 |

(Continued)

FOREIGN PATENT DOCUMENTS

| | | |
|---|---|---|
| KR | 10-2007-0058776 A | 6/2007 |
| WO | 02/064132 A2 | 8/2002 |
| WO | 2008/144888 A1 | 12/2008 |

OTHER PUBLICATIONS

Ahmad, et al. "Solid-Nanoemulsion Preconcentrate for Oral Delivery of Paclitaxel: Formulation Design, Biodistribution, and y Scintigraphy Imaging", BioMed Research International. Jul. 2014, vol. 2014, pp. 1-12.

(Continued)

*Primary Examiner* — Dominic Lazaro
(74) *Attorney, Agent, or Firm* — Vorys, Sater, Seymour & Pease LLP; Mih Suhn Koh

(57) ABSTRACT

Provided is a pharmaceutical composition for oral administration, including (a) a taxane, (b) a medium chain triglyceride, (c) an oleoyl glycerol complex having 30 to 65% by weight of monooleoyl glycerol contents; 15 to 50% by weight of dioleoyl glycerol contents; and 2 to 20% by weight of trioleoyl glycerol contents, (d) a surfactant, and optionally (e) polyoxyl glyceryl fatty acid ester and a process for preparing the same.

4 Claims, 4 Drawing Sheets

(51) Int. Cl.
*A61P 35/00* (2006.01)
*A61K 9/107* (2006.01)

(52) U.S. Cl.
CPC ............ *A61K 9/4858* (2013.01); *A61K 47/14* (2013.01); *A61K 47/26* (2013.01); *A61K 47/44* (2013.01); *A61P 35/00* (2018.01); *A61K 9/107* (2013.01)

(56) References Cited

U.S. PATENT DOCUMENTS

| | | | | |
|---|---|---|---|---|
| 2005/0025792 | A1* | 2/2005 | Peracchia | A61K 9/1075 424/400 |
| 2006/0104999 | A1 | 5/2006 | Chung et al. | |
| 2006/0127420 | A1 | 6/2006 | Chung et al. | |
| 2010/0273728 | A1 | 10/2010 | Wasan et al. | |
| 2011/0033413 | A1* | 2/2011 | Kwetkat | A61K 8/0208 424/78.03 |
| 2011/0104268 | A1* | 5/2011 | Pachot | A61K 9/1075 424/452 |
| 2014/0228308 | A1 | 8/2014 | Wasan et al. | |

OTHER PUBLICATIONS

Huizing et al., "Taxanes: A New Class of Antitumor Agents", Cancer Inv., 1995, 13: 381-404.
Suffness (Ed.), Taxol Science and Applications, CRC Press (1995).
Walle et al., "Taxol Transport by Human Intestinal Epithelial Caco-2 Cells", Drug Metabo. Disp., 26(4): 343-346 (1998).

\* cited by examiner (A)        (B)

(A)  (B)

PHARMACEUTICAL COMPOSITION FOR ORAL ADMINISTRATION COMPRISING TAXANE

TECHNICAL FIELD

The present invention relates to a pharmaceutical composition for oral administration comprising a taxane as an anticancer agent. More specifically, the present invention relates to a taxane-containing pharmaceutical composition for oral administration comprising an oleoyl glycerol complex and optionally polyoxyl glyceryl fatty acid ester.

BACKGROUND ART

Taxanes, which are an anticancer agent showing their anti-proliferative effect by acting on the organization of the microtubules in the cellular cytoskeletal system (Huizing M. T. et al., Cancer Inv., 1995, 13: 381-404), are known to exhibit excellent cytotoxicity against various kinds of cancers such as ovarian cancer, breast cancer, esophagus cancer, melanoma and leukemia. Parenteral dosage forms of paclitaxel and docetaxel are commercially available under the trademarks Taxol™ and Taxotere™, respectively. Since a taxane is known to have very low water solubility, the currently available paclitaxel-containing formulation, e.g., Taxol™, has been formulated into the form of emulsion preconcentrate, which is diluted before using for injection. However, in order to overcome the problems related to patient compliance due to the use of the injection form, stability of the formulation, and safety to the human body, etc., researches on the formulations for oral administration are being carried out.

Meanwhile, it has been reported that the oral administration of a taxane such as paclitaxel exhibits very low oral bioavailability due to the action of an outwardly directed efflux pump (Walle et al, Drug Metabo. Disp. 26(4): 343-346 (1998)). It has been also reported that the orally administered paclitaxel is very poorly absorbed (less than 1%) (Eiseman et al, Second NCI Workshop on Taxol and Taxus (sept. 1992), Suffness (ed.) et al, Taxol™ Science and Applications, CRC Press (1995)). As an attempt to improve such a low oral bioavailability, Korean Patent Publication No. 10-2004-0009015 has disclosed a solubilized taxane-containing composition for oral administration, which is formulated by using a medium chain triglyceride such as triacetin, a monoglyceride such as monoolein, and a surfactant such as Tween. Said composition is a solubilized taxane-containing composition for oral administration, whose bioavailability is increased through high mucoadhesive property in the intestine by the monoglyceride such as monoolein. And also, Korean Patent Publication No. 10-2007-0058776 has disclosed an improved process for preparing the solubilized taxane-containing composition for oral administration, the process comprising dissolving paclitaxel, along with a medium chain triglyceride, a monoglyceride, and surfactant, in an organic solvent.

Solid formulations such as soft capsules have advantages in terms of the ease of use, compared to the lipid solution form. Considering the patient's compliance, it is necessary to control the size of the soft capsules to an appropriate size. Therefore, in order to prepare a soft capsule containing the therapeutically effective amount of a taxane, it is required to prepare a lipid solution containing the taxane in a high concentration. However, when a taxane is contained in a high concentration (for example, 4% by weight or more) according to conventional formulation methods (e.g., Korean Patent Publication Nos. 10-2004-0009015 and 10-2007-0058776), the taxane is precipitated from the lipid solution and thus the completely solubilized lipid solution cannot be obtained, thereby leading to the problem of decreased bioavailability.

DISCLOSURE

Technical Problem

A conventional solubilized paclitaxel-containing compositions for oral administration, for example the composition prepared according to Korean Patent Publication Nos. 10-2004-0009015 and 10-2007-0058776, is stored under refrigerated conditions in the semi-solid form, which is converted into a solution form at the time of use and then is orally administered to a patient. However, the composition stored under refrigerated conditions in the semi-solid form is not converted to a solution at room temperature, and also still exists in the semi-solid form even when it is allowed to stand for a long time. Therefore, in order to convert to the solution form that can be administered to a patient, there is a problem that additional processing through heating should be performed.

The present inventors carried out various researches in order to solve the problems. Surprisingly, the present inventors have found that, when formulation processes are performed by using a certain oleoyl glycerol complex instead of the monoglyceride, the resulting formulations are present in a solution form at room temperature and thus can be administered directly to a patient without additional processing such as heating. In addition, the present inventors have found that the compositions formulated by using the oleoyl glycerol complex effectively allow to increase the in vivo absorption rate, in comparison with the conventional composition obtained by using a monoglyceride such as monoolein.

An also, the present inventors have found that, when formulation processes are performed by adding polyoxyl glyceryl fatty acid ester additionally, a clear solution containing a taxane in a high concentration can be obtained, thereby being able to be formulated into a soft capsule form without the formation of a precipitate. In addition, it has been found that the resulting soft capsules are quickly absorbed from the beginning and represent a remarkably increased in vivo absorption rate.

Therefore, it is an object of the present invention to provide a taxane-containing pharmaceutical composition for oral administration which is formulated by using said oleoyl glycerol complex and optionally polyoxyl glyceryl fatty acid ester.

And also, it is another object of the present invention to provide a process for preparing the pharmaceutical composition for oral administration.

Technical Solution

In accordance with an aspect of the present invention, there is provided a pharmaceutical composition for oral administration, comprising (a) a taxane, (b) a medium chain triglyceride, (c) an oleoyl glycerol complex having 30 to 65% by weight of monooleoyl glycerol contents; 15 to 50% by weight of dioleoyl glycerol contents; and 2 to 20% by weight of trioleoyl glycerol contents, and (d) a surfactant.

In an embodiment, the oleoyl glycerol complex has 32 to 52% by weight of monooleoyl glycerol contents; 30 to 50% by weight of dioleoyl glycerol contents; and 5 to 20% by weight of trioleoyl glycerol contents. In another embodiment, the oleoyl glycerol complex has 55 to 65% by weight of monooleoyl glycerol contents; 15 to 35% by weight of dioleoyl glycerol contents; and 2 to 10% by weight of trioleoyl glycerol contents. In still another embodiment, the pharmaceutical composition for oral administration may further comprise polyoxyl glyceryl fatty acid ester, along with a taxane in a high concentration.

In accordance with another aspect of the present invention, there is provided a process for preparing a pharmaceutical composition for oral administration, comprising (i) dissolving a taxane and a medium chain triglyceride in an organic solvent, and (ii) removing the organic solvent from the solution obtained in Step (i), followed by mixing an oleoyl glycerol complex having 30 to 65% by weight of monooleoyl glycerol contents; 15 to 50% by weight of dioleoyl glycerol contents; and 2 to 20% by weight of trioleoyl glycerol contents, and a surfactant therewith.

In accordance with still another aspect of the present invention, there is provided a process for preparing a pharmaceutical composition for oral administration, comprising (i') dissolving a taxane, a medium chain triglyceride, an oleoyl glycerol complex having 30 to 65% by weight of monooleoyl glycerol contents; 15 to 50% by weight of dioleoyl glycerol contents; and 2 to 20% by weight of trioleoyl glycerol contents, and a surfactant in an organic solvent, and (ii') removing the organic solvent from the solution obtained in Step (i').

In accordance with still another aspect of the present invention, there is provided a process for preparing a pharmaceutical composition for oral administration, comprising (i") dissolving a taxane and polyoxyl glyceryl fatty acid ester in an organic solvent, (ii") removing the organic solvent from the solution obtained in Step (i"), followed by mixing a medium chain triglyceride, an oleoyl glycerol complex having 30 to 65% by weight of monooleoyl glycerol contents; 15 to 50% by weight of dioleoyl glycerol contents; and 2 to 20% by weight of trioleoyl glycerol contents, and a surfactant therewith to form a solution, and (iii") optionally, filling the solution obtained in Step (ii") in a soft capsule.

In accordance with still another aspect of the present invention, there is provided a process for preparing a pharmaceutical composition for oral administration, comprising (i'") dissolving a taxane, a medium chain triglyceride, an oleoyl glycerol complex having 30 to 65% by weight of monooleoyl glycerol contents; 15 to 50% by weight of dioleoyl glycerol contents; and 2 to 20% by weight of trioleoyl glycerol contents, a surfactant, and polyoxyl glyceryl fatty acid ester in an organic solvent, (ii'") removing the organic solvent from the solution obtained in Step (i'"), and (iii'") optionally, filling the solution obtained in Step (ii'") in a soft capsule.

Advantageous Effects

It has been found by the present invention that a solubilized taxane-containing composition for oral administration remarkably varies in the form and/or appearance thereof according to the types and/or properties of the lipid used. Especially, it has been found by the present invention that, when formulation processes are performed by using a certain oleoyl glycerol complex, the resulting formulations are present in a solution form at room temperature and thus can be administered directly to a patient without additional processing such as heating. In addition, it has been found by the present invention that the compositions formulated by using the oleoyl glycerol complex effectively allow to increase the in vivo absorption rate, in comparison with the conventional composition obtained by using a monoglyceride such as monoolein. An also, it has been found by the present invention that, when formulation processes are performed by adding polyoxyl glyceryl fatty acid ester additionally, a clear solution containing a taxane in a high concentration can be obtained, thereby being able to be formulated into a soft capsule form without the formation of a precipitate. Especially it has been found by the present invention that the resulting soft capsules are quickly absorbed from the beginning and represent a remarkably increased in vivo absorption rate. Therefore, the pharmaceutical composition for oral administration according to the present invention can solve the problems of the conventional formulations that additional solubilizing processing should be carried out at the time of use; and effectively increase the in vivo absorption rate of the taxane.

BEST MODE

Figure 1:
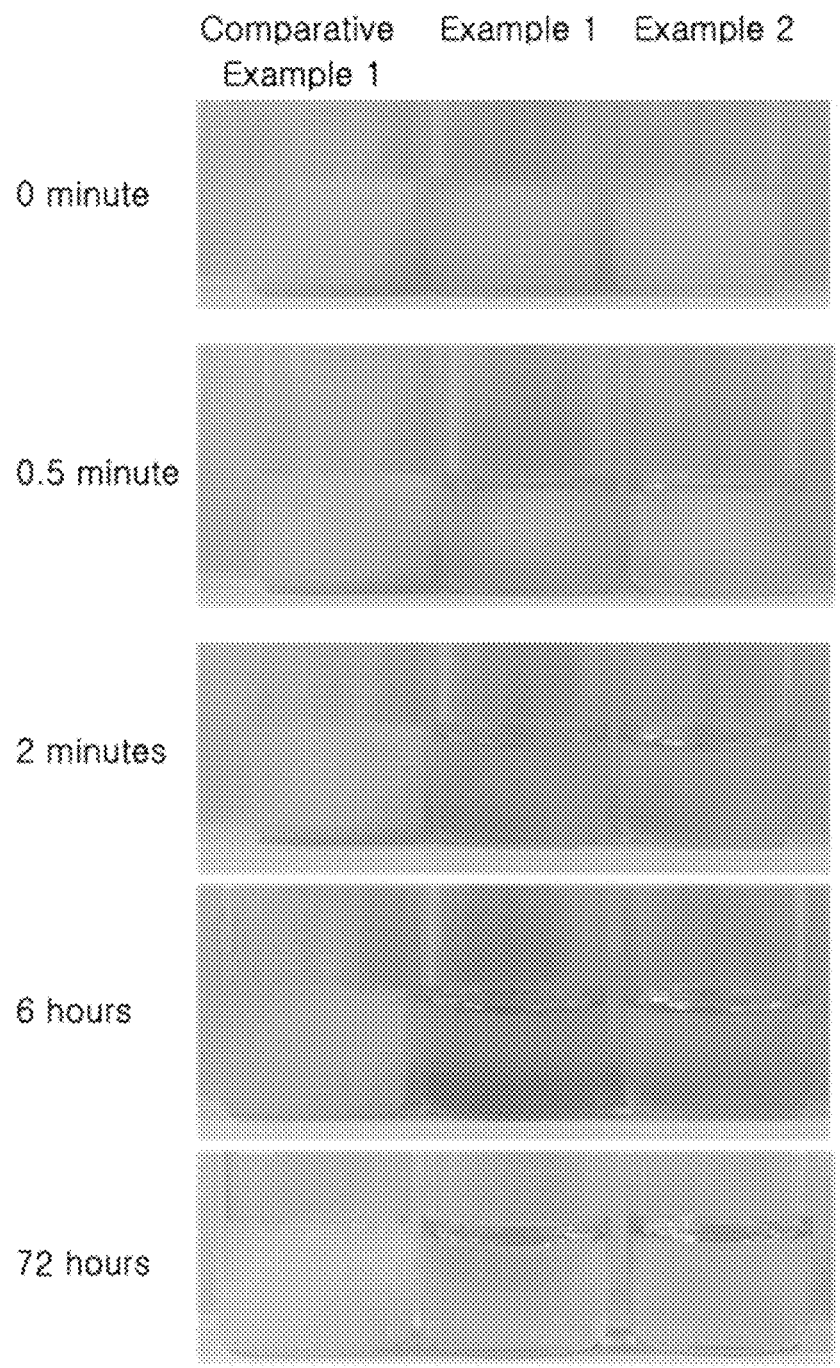
FIG. 1 represents the appearances obtained by storing the paclitaxel-containing pharmaceutical compositions for oral administration prepared in Example 1, Example 2 and Comparative Example 1 at 4° C. for 8 hours, followed by being allowed to stand at 25° C. for 72 hours.

The present invention provides a pharmaceutical composition for oral administration, comprising (a) a taxane, (b) a medium chain triglyceride, (c) an oleoyl glycerol complex having 30 to 65% by weight of monooleoyl glycerol contents; 15 to 50% by weight of dioleoyl glycerol contents; and 2 to 20% by weight of trioleoyl glycerol contents, and (d) a surfactant.

It has been found by the present invention that a solubilized taxane-containing composition for oral administration remarkably varies in the form and/or appearance thereof according to the types and/or properties of the lipid used. Especially, it has been found by the present invention that, when formulation processes are performed by using a certain oleoyl glycerol complex, the resulting formulations are present in a solution form at room temperature and thus can be administered directly to a patient without additional processing such as heating. In addition, it has been found by the present invention that the compositions formulated by using the oleoyl glycerol complex effectively allow to increase the in vivo absorption rate, in comparison with the conventional composition obtained by using a monoglyceride such as monoolein.

As used herein, the term "oleoyl glycerol complex" refers to a mixture obtained by partial glycerolysis of vegetable oils mainly containing triacylglycerols of oleic acid or by esterification of glycerol by oleic acid. The respective contents of monooleoyl glycerol, dioleoyl glycerol and trioleoyl glycerol therein vary according to the partial glycerolysis and/or esterification. An oleoyl glycerol complex having a certain content ratio is used in the present invention. That is, there is used in the present invention an oleoyl glycerol complex having 30 to 65% by weight of monooleoyl glycerol contents; 15 to 50% by weight of dioleoyl glycerol contents; and 2 to 20% by weight of trioleoyl glycerol contents. In an embodiment, the oleoyl glycerol complex has 32 to 52% by weight of monooleoyl glycerol contents; 30 to 50% by weight of dioleoyl glycerol contents; and 5 to 20% by weight of trioleoyl glycerol contents. In another embodiment, the oleoyl glycerol complex has 55 to 65% by weight of monooleoyl glycerol contents; 15 to 35% by weight of dioleoyl glycerol contents; and 2 to 10% by weight of trioleoyl glycerol contents. In addition, a commercially available oleoyl glycerol complex having said content ratio, e.g., PECEOL™ (Gattefosse) or CAPMUL™ (Abitec) may be also used.

In the pharmaceutical composition for oral administration of the present invention, the taxane includes one or more selected from the group consisting of paclitaxel, docetaxel, 7-epipaclitaxel, t-acetylpaclitaxel, 10-desacetylpaclitaxel, 10-desacetyl-7-epipaclitaxel, 7-xylosylpaclitaxel, 10-desacetyl-7-glutarylpaclitaxel, 7-N,N-dimethylglycylpaclitaxel, 7-L-alanylpaclitaxel, and so on. For example, the taxane may be paclitaxel and/or docetaxel.

The medium chain triglyceride means a substance in which three molecules of saturated or unsaturated $C_2$-$C_{20}$ fatty acids and one molecule of glycerol are linked by ester bond. For example, the medium chain triglyceride includes triacetin, tripropionin, tributyrin, trivalerin, tricaproin, tricaprylin (e.g., Captex™ 8000 etc.), tricaprin, triheptanoin, trinonanoin, triundecanoin, trilaurin, tritridecanoin, trimyristin, tripentadecanoin, tripalmitin, glyceryl triheptadecanoate, triolein, and so on.

The surfactant includes polyoxyethylene-polyoxypropylene block copolymer (e.g., Poloxamer™), sorbitan ester (e.g., Span™), polyoxyethylene sorbitan (e.g., Tween™), polyoxyethylene ether (e.g., Brij™), and so on.

In an embodiment, the pharmaceutical composition of the present invention may comprise 0.5 to 1.5% by weight of the taxane, 20 to 35% by weight of the medium chain triglyceride, 45 to 60% by weight of the oleoyl glycerol complex, and 15 to 25% by weight of the surfactant. Preferably, the pharmaceutical composition of the present invention may comprise 0.8 to 1.2% by weight of the taxane, 25 to 30% by weight of the medium chain triglyceride, 50 to 55% by weight of the oleoyl glycerol complex, and 15 to 20% by weight of the surfactant.

It has been found by the present invention that, when formulation processes are performed by adding polyoxyl glyceryl fatty acid ester additionally, a clear solution containing a taxane in a high concentration can be obtained, thereby being able to be formulated into a soft capsule form without the formation of a precipitate. Especially it has been found by the present invention that the resulting soft capsules are quickly absorbed from the beginning and represent a remarkably increased in vivo absorption rate.

Therefore, the pharmaceutical composition for oral administration of the present invention may further comprise polyoxyl glyceryl fatty acid ester. The polyoxyl glyceryl fatty acid ester may be one or more selected from the group consisting of caprylocaproyl polyoxyl glyceride, lauroyl polyoxyl glyceride, and stearoyl polyoxyl glyceride.

Preferably, the polyoxyl glyceryl fatty acid ester may be one or more selected from the group consisting of caprylocaproyl polyoxyl-32 glyceride (e.g., LABRASOL™, etc.), lauroyl polyoxyl-32 glyceride (e.g., Gelucire™ 44/14, etc.), and stearoyl polyoxyl-32 glyceride (e.g., Gelucire™ 50/13, etc.). In an embodiment, the pharmaceutical composition for oral administration of the present invention may comprise 4 to 40% by weight of the taxane, 10 to 30% by weight of the medium chain triglyceride, 30 to 70% by weight of the oleoyl glycerol complex, 5 to 30% by weight of the surfactant, and 10 to 30% by weight of polyoxyl glyceryl fatty acid ester. In another embodiment, the pharmaceutical composition for oral administration of the present invention may comprise 4 to 25% by weight of the taxane, 10 to 20% by weight of the medium chain triglyceride, 40 to 60% by weight of the oleoyl glycerol complex, 10 to 25% by weight of the surfactant, and 10 to 20% by weight of polyoxyl glyceryl fatty acid ester. The pharmaceutical composition for oral administration is preferably in the form filled in a soft capsule.

In another aspect of the present invention, there is provided a process for preparing a pharmaceutical composition for oral administration, comprising (i) dissolving a taxane and a medium chain triglyceride in an organic solvent, and (ii) removing the organic solvent from the solution obtained in Step (i), followed by mixing an oleoyl glycerol complex having 30 to 65% by weight of monooleoyl glycerol contents; 15 to 50% by weight of dioleoyl glycerol contents; and 2 to 20% by weight of trioleoyl glycerol contents, and a surfactant therewith.

In still another aspect of the present invention, there is provided a process for preparing a pharmaceutical composition for oral administration, comprising (i') dissolving a taxane, a medium chain triglyceride, an oleoyl glycerol complex having 30 to 65% by weight of monooleoyl glycerol contents; 15 to 50% by weight of dioleoyl glycerol contents; and 2 to 20% by weight of trioleoyl glycerol contents, and a surfactant in an organic solvent, and (ii') removing the organic solvent from the solution obtained in Step (i').

In still another aspect of the present invention, there is provided a process for preparing a pharmaceutical composition for oral administration, comprising (i") dissolving a taxane and polyoxyl glyceryl fatty acid ester in an organic solvent, (ii") removing the organic solvent from the solution obtained in Step (i"), followed by mixing a medium chain triglyceride, an oleoyl glycerol complex having 30 to 65% by weight of monooleoyl glycerol contents; 15 to 50% by weight of dioleoyl glycerol contents; and 2 to 20% by weight of trioleoyl glycerol contents, and a surfactant therewith to form a solution, and (iii") optionally, filling the solution obtained in Step (ii") in a soft capsule.

In still another aspect of the present invention, there is provided a process for preparing a pharmaceutical composition for oral administration, comprising (i''') dissolving a taxane, a medium chain triglyceride, an oleoyl glycerol complex having 30 to 65% by weight of monooleoyl glycerol contents; 15 to 50% by weight of dioleoyl glycerol contents; and 2 to 20% by weight of trioleoyl glycerol contents, a surfactant, and polyoxyl glyceryl fatty acid ester in an organic solvent, (ii''') removing the organic solvent from the solution obtained in Step (i'''), and (iii''') optionally, filling the solution obtained in Step (ii''') in a soft capsule.

In the processes of the present invention, said oleoyl glycerol complex, taxane, medium chain triglyceride, surfactant, and polyoxyl glyceryl fatty acid ester are as described above.

In the processes of the present invention, the organic solvent may be one or more selected from the group consisting of a halogenated alkyl compound, an alcohol, and a ketone. The halogenated alkyl compound may be one or more selected from the group consisting of halogenated $C_1$ to $C_5$ alkyl compounds, preferably methylene chloride or chloroform, more preferably methylene chloride. The alcohol may be one or more selected from the group consisting of $C_1$ to $C_5$ lower alcohols, preferably methanol, ethanol or isopropyl alcohol, more preferably ethanol. The ketone may be acetone.

The organic solvent may be used in an amount capable of dissolving the taxane and the medium chain triglyceride, preferably in the amount of 0.4 times to 20 times based on the volume of the medium chain triglyceride, more preferably in the same volume as the volume of the medium chain triglyceride, but is not limited thereto. Said amounts of the organic solvent, which makes it possible to dissolve the taxane such as paclitaxel and docetaxel sufficiently, can reduce the waste originated from the use of excessive amounts of the solvent and the unnecessary effort for removing the organic solvent. In the processes of the present invention, the step for removing the organic solvent may be performed according to conventional drying methods, for example, by drying under reduced pressure at 15 to 50° C., preferably at room temperature. Through performing the steps for dissolving with an organic solvent and removing the organic solvent as described above, it is possible to homogeneously mix the respective components in the resulting composition.

The present invention will be described in further detail with reference to the following examples and experimental examples. These examples and experimental examples are for illustrative purposes only and are not intended to limit the scope of the present invention.

Example 1

The paclitaxel-containing pharmaceutical composition for oral administration was prepared according to the components and amounts shown in Table 1. Paclitaxel (0.174 g) and tricaprylin (4.75 g) were dissolved in methylene chloride (2.18 mL). The resulting solution was dried under reduced pressure at 40° C. to remove methylene chloride. To the resulting mixture, were added PECEOL™ (Gattefosse) (9.42 g) and Tween™ 80 (3.225 g). The resulting mixture was stirred at about 40° C. to obtain the pharmaceutical composition in the form of a clear viscous solution.

TABLE 1

| L/I | Component | Amount (g) | Ratio (% by weight) |
|---|---|---|---|
| 1 Taxane | Paclitaxel | 0.174 | 0.99 |
| 2 Medium chain triglyceride | Tricaprylin | 4.75 | 27.03 |
| 3 Oleoyl glycerol complex | PECEOL ™ | 9.42 | 53.62 |
| 4 Surfactant | Tween ™ 80 | 3.225 | 18.36 |
| Total | | 17.569 | 100.00 |

Example 2

The paclitaxel-containing pharmaceutical composition for oral administration was prepared in accordance with the same procedures as in Example 1, using anhydrous ethanol (3.49 mL) instead of methylene chloride.

Example 3

Paclitaxel (0.174 g), tricaprylin (4.75 g), PECEOL™ (9.42 g) and Tween™ 80 (3.225 g) were dissolved in methylene chloride (2.18 mL). The resulting solution was dried under reduced pressure at 40° C. to remove methylene chloride. The resulting mixture was stirred at about 40° C. to obtain the pharmaceutical composition in the form of a clear viscous solution.

Example 4

The paclitaxel-containing pharmaceutical composition for oral administration was prepared in accordance with the same procedures as in Example 3, using anhydrous ethanol (3.49 mL) instead of methylene chloride.

Example 5

The docetaxel-containing pharmaceutical composition for oral administration was prepared in accordance with the same procedures as in Example 1, using docetaxel (0.174 g) instead of paclitaxel.

Example 6

The docetaxel-containing pharmaceutical composition for oral administration was prepared in accordance with the same procedures as in Example 5, using anhydrous ethanol (3.49 mL) instead of methylene chloride.

Example 7

The docetaxel-containing pharmaceutical composition for oral administration was prepared in accordance with the same procedures as in Example 3, using docetaxel (0.174 g) instead of paclitaxel.

Example 8

The docetaxel-containing pharmaceutical composition for oral administration was prepared in accordance with the same procedures as in Example 7, using anhydrous ethanol (3.49 mL) instead of methylene chloride.

Example 9

The paclitaxel-containing pharmaceutical composition for oral administration was prepared in accordance with the same procedures as in Example 1, using Capmul™ GMO-50 EP/NF (Abitec) (9.42 g) instead of PECEOL™.

Example 10

The paclitaxel-containing pharmaceutical composition for oral administration was prepared in accordance with the same procedures as in Example 9, using anhydrous ethanol (3.49 mL) instead of methylene chloride.

Example 11

The paclitaxel-containing pharmaceutical composition for oral administration was prepared in accordance with the same procedures as in Example 1, using triacetin (Sigma) instead of tricaprylin.

Example 12

The paclitaxel-containing pharmaceutical composition for oral administration was prepared in accordance with the same procedures as in Example 1, using tripropionin (Sigma) instead of tricaprylin.

Example 13

The paclitaxel-containing pharmaceutical composition for oral administration was prepared in accordance with the same procedures as in Example 1, using tributyrin (Sigma) instead of tricaprylin.

Example 14

The paclitaxel-containing pharmaceutical composition for oral administration was prepared in accordance with the same procedures as in Example 1, using trivalerin (Sigma) instead of tricaprylin.

Example 15

The paclitaxel-containing pharmaceutical composition for oral administration was prepared in accordance with the same procedures as in Example 1, using tricaproin (Sigma) instead of tricaprylin.

Example 16

The paclitaxel-containing pharmaceutical composition for oral administration was prepared in accordance with the same procedures as in Example 1, using triheptanoin (Sigma) instead of tricaprylin.

Example 17

The paclitaxel-containing pharmaceutical composition for oral administration was prepared in accordance with the same procedures as in Example 1, using trinonanoin (Sigma) instead of tricaprylin.

Example 18

The paclitaxel-containing pharmaceutical composition for oral administration was prepared in accordance with the same procedures as in Example 1, using tricaprin (Sigma) instead of tricaprylin.

Example 19

The paclitaxel-containing pharmaceutical composition for oral administration was prepared in accordance with the same procedures as in Example 1, using triundecanoin (Sigma) instead of tricaprylin.

Example 20

The paclitaxel-containing pharmaceutical composition for oral administration was prepared in accordance with the same procedures as in Example 1, using trilaurin (Sigma) instead of tricaprylin.

Example 21

The paclitaxel-containing pharmaceutical composition for oral administration was prepared in accordance with the same procedures as in Example 1, using tritridecanoin (Sigma) instead of tricaprylin.

Example 22

The paclitaxel-containing pharmaceutical composition for oral administration was prepared in accordance with the same procedures as in Example 1, using trimyristin (Sigma) instead of tricaprylin.

Example 23

The paclitaxel-containing pharmaceutical composition for oral administration was prepared in accordance with the same procedures as in Example 1, using tripentadecanoin (Sigma) instead of tricaprylin.

Example 24

The paclitaxel-containing pharmaceutical composition for oral administration was prepared in accordance with the same procedures as in Example 1, using tripalmitin (Sigma) instead of tricaprylin.

Example 25

The paclitaxel-containing pharmaceutical composition for oral administration was prepared in accordance with the same procedures as in Example 1, using glyceryl triheptadecanoate (Sigma) instead of tricaprylin.

Example 26

The paclitaxel-containing pharmaceutical composition for oral administration was prepared in accordance with the same procedures as in Example 1, using triolein (Sigma) instead of tricaprylin.

Comparative Example 1. Preparation of Paclitaxel-Containing Pharmaceutical Composition for Oral Administration Comprising Monoolein According to Korean Patent Publication No. 10-2007-0058776, the paclitaxel-containing pharmaceutical composition for oral administration was prepared by using monoolein as a lipid. That is, paclitaxel (0.174 g) and tricaprylin (4.75 g) were dissolved in methylene chloride (2.18 mL). The resulting solution was dried under reduced pressure at 40° C. to remove methylene chloride. To the resulting mixture, were added monoolein (9.4 g) and Tween™ 80 (3.225 g). The resulting mixture was stirred at about 40° C. to obtain the pharmaceutical composition in the form of a clear viscous solution. The monoolein has 96.12% by weight of monooleoyl glycerol contents and 3.88% by weight of dioleoyl glycerol contents.

Experimental Example 1: Evaluation of Appearance of the Formulations According to Temperature Conditions (1) Evaluation at the Condition of 25° C. after Refrigerated Storage The paclitaxel-containing pharmaceutical compositions for oral administration prepared in Example 1, Example 2 and Comparative Example 1 were stored at 4° C. for 8 hours and then allowed to stand at 25° C. for 72 hours. The resulting appearances thereof are shown in FIG. 1. As shown in FIG. 1, the formulations of both Example 1 and Example 2 were changed to a clear solution, which can be taken by a patient, at 25° C. within two minutes. In contrast, the formulation of Comparative Example 1 was not changed to a solution at room temperature (about 25° C.). Even when the formulation of Comparative Example 1 was allowed to stand over 72 hours, the appearance of a semi-solid form was still maintained.

(2) Evaluation at the Condition of 15° C. after Melting

Figure 2:
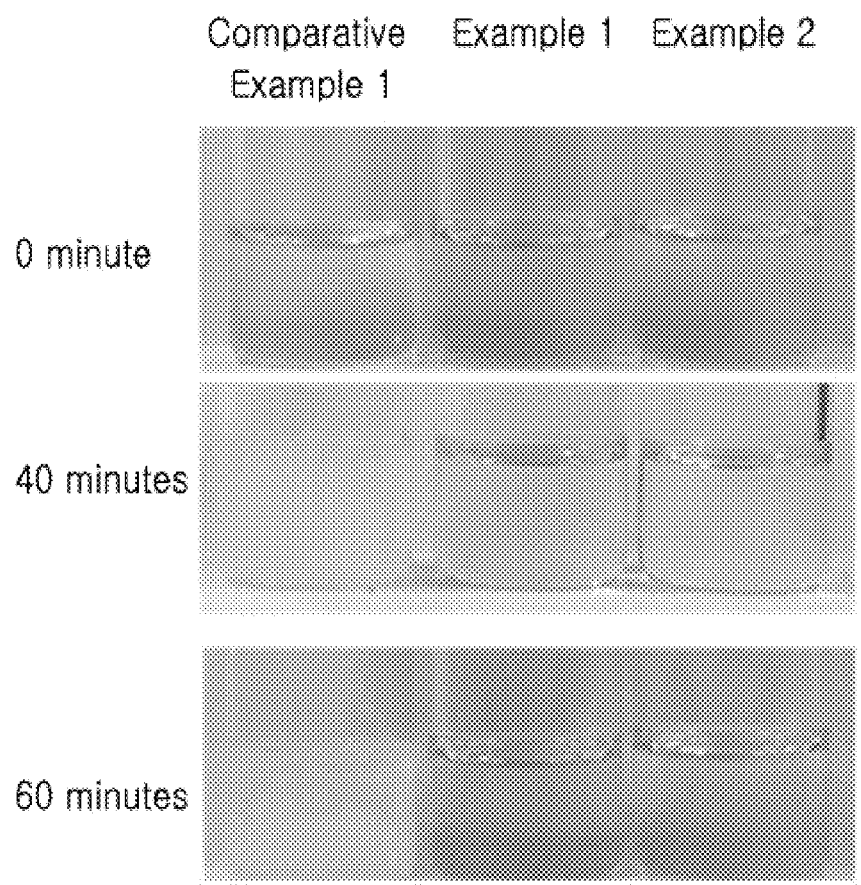
FIG. 2 represents the appearances obtained by storing the paclitaxel-containing pharmaceutical compositions for oral administration prepared in Example 1, Example 2 and Comparative Example 1 at 4° C. for 8 hours, followed by melting the formulations at 50° C. and then being allowed to stand at 15° C. for 1 hour.

The paclitaxel-containing pharmaceutical compositions for oral administration prepared in Example 1, Example 2 and Comparative Example 1 were stored at 4° C. for 8 hours and then completely melted at 50° C. When the respective formulations were allowed to stand at 15° C. for 1 hour, the resulting appearances thereof are shown in FIG. 2. As shown in FIG. 2, the formulations of Example 1 and Example 2 maintained the clear solution, which can be taken by a patient, even after 1 hour at 15° C. In contrast, the formulation of Comparative Example 1 was solidified.

Experimental Example 2. Evaluation of In Vivo Absorption Rate

The paclitaxel-containing pharmaceutical compositions for oral administration prepared in Example 1 and Comparative Example 1 were orally administered in the dose of 50 mg/kg to ICR mice (6 week old, female, Orient Bio, Republic of Korea), using a gastric zonde, respectively. The formulation of Comparative Example 1 was completely melted at 50° C. after the preparation thereof and then administered immediately. At 0 minute, 30 minutes, 1 hour, 2 hours, 4 hours, 6 hours and 8 hours after the drug administration, the blood samples were taken from the orbital veins of the mice and then centrifuged at 8,000×g for 20 minutes to obtain the plasma samples, which were stored at −70° C.

The plasma samples were melted through being allowed to stand at room temperature and then stirred with a vortex mixer for 1 minute. The internal standard solution (paclitaxel-$d_5$ 2.50 μg/mL, in methanol) (10.0 μL) was added to the plasma samples (50.0 μL), which were stirred for 3 minutes and then centrifuged at 4,000×g for about 1 minute. Acetonitrile (200 μL) was added to the samples, which were stirred for 3 minutes and then centrifuged at 4,000×g for about 1 minute. Each supernatant (100 μL) was taken therefrom and then distilled water (100 μL) containing 0.1% (v/v) formic acid was added thereto. Each resulting mixture was stirred for 3 minutes and then centrifuged at 4,000×g at room temperature for about 1 minute. Each supernatant (20.0 μL) was taken and then subject to the UPLC-MS/MS analysis.

The conditions for UPLC-MS/MS analysis are as follows.
UPLC: UPLC, Waters ACQUITY UPLC™ System, Waters
Detector: Waters Xevo™ TQMS, Waters
Column: Waters ACQUITY UPLC™ BEHC18, 1.7 um (2.1 mmID×50 mmL)
Data processor: MassLynx V4.1, Waters
Mobile phase: 0.1% (v/v) FA in DW: 0.1% (v/v) FA in ACN (50:50, v/v)
(FA: formic acid, DW: distilled water, ACN: acetonitrile)
Flow rate: 0.4 mL/minute
Detector condition: ESI+, MRM mode

| L/I | Compound | Observed transition (m/z) | Cone voltage (V) | Collision energy (eV) |
|---|---|---|---|---|
| Analyte | Paclitaxel | 854.67→286.21 | 20 | 20 |
| Internal standard | Paclitaxel-$d_5$ | 859.63→291.26 | 20 | 20 |

The pharmacokinetic parameters calculated from the blood concentrations of paclitaxel measured in the above are shown in Table 2.

TABLE 2

| | Comparative Example 1 | Example 1 |
|---|---|---|
| $C_{max}$ (ng/ml) | 2945.25 | 5443.075 |
| $T_{max}$ (hour) | 2 | 2 |
| $AUC_{0-8\ hr}$ (ng · hr/ml) | 15023.98 | 20208.83 |
| $AUC_{0-inf}$ (ng · hr/ml) | 17357.07 | 21195.84 |

From the results of Table 2, it can be seen that the paclitaxel-containing pharmaceutical composition for oral administration according to the present invention exhibited remarkably increased in vivo absorption rate, in comparison with the conventional formulation.

Example 27. Docetaxel-Containing Soft Capsules

Figure 3:
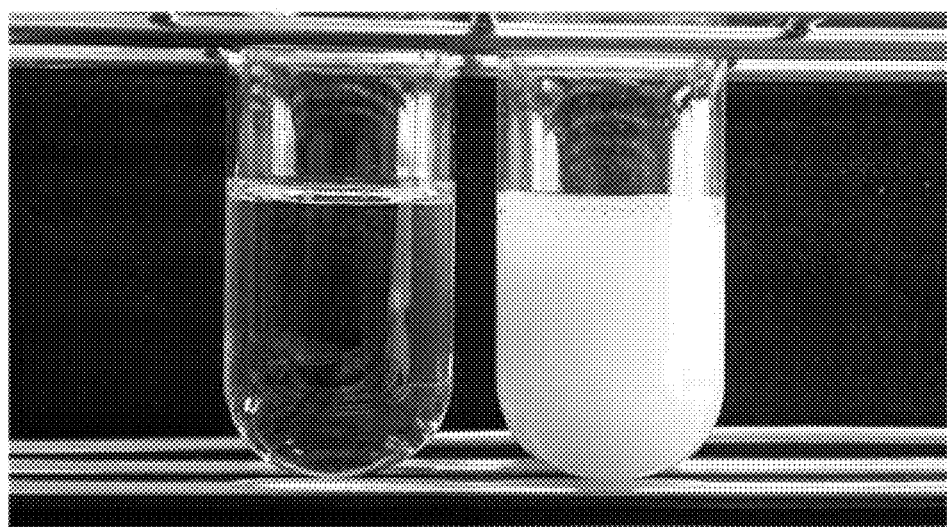
FIG. 3 represents the appearances of the docetaxel-containing lipid solution prepared in Example 27 and Comparative Example 2. A: the docetaxel-containing lipid solution prepared in Example 27, B: the docetaxel-containing lipid solution prepared in Comparative Example 2.

The docetaxel-containing pharmaceutical composition for oral administration was prepared according to the components and amounts shown in Table 3. Docetaxel and LABRASOL™ (Gattefosse) were completely dissolved in ethanol (about 14 times of the volume of tricaprylin). The resulting solution was dried under reduced pressure at 40° C. to remove ethanol. To the resulting mixture, were added tricaprylin (Captex™ 8000, ABITEC), PECEOL™ (Gattefosse), and Tween™ 80. The resulting mixture was stirred at 40° C. to obtain the clear oily solution. The resulting clear oily solution was filled into a soft capsule. The appearance of the clear oily solution is shown in FIG. 3 (left, A).

TABLE 3

| L/I | Component | | Amount/ 1 capsule | Ratio (% by weight) |
|---|---|---|---|---|
| 1 | Taxane | Docetaxel | 50 mg | 4.84 |
| 2 | Medium chain triglyceride | Tricaprylin | 0.14 ml | 12.77 |
| 3 | Oleoyl glycerol complex | PECEOL ™ | 0.56 ml | 50.65 |
| 4 | Surfactant | Tween ™ 80 | 0.16 ml | 17.42 |
| 5 | Polyoxyl glyceryl fatty acid ester | LABRASOL ™ | 0.14 ml | 14.32 |
| | Total | | | 100.00 |

Example 28

The docetaxel-containing pharmaceutical composition for oral administration in the soft capsule form was prepared in accordance with the same procedures as in Example 27, using Gelucire™ 44/14 (Gettafosse) instead of LABRASOL™.

Example 29

The docetaxel-containing pharmaceutical composition for oral administration in the soft capsule form was prepared in accordance with the same procedures as in Example 27, using Gelucire™ 50/13 (Gettafosse) instead of LABRASOL™.

Example 30

The docetaxel-containing pharmaceutical composition for oral administration in the soft capsule form was prepared in accordance with the same procedures as in Example 27, using triacetin (Sigma) instead of tricaprylin.

Example 31

The docetaxel-containing pharmaceutical composition for oral administration in the soft capsule form was prepared in accordance with the same procedures as in Example 27, using tripropionin (Sigma) instead of tricaprylin.

Example 32

The docetaxel-containing pharmaceutical composition for oral administration in the soft capsule form was prepared in accordance with the same procedures as in Example 27, using tributyrin (Sigma) instead of tricaprylin.

Example 33

The docetaxel-containing pharmaceutical composition for oral administration in the soft capsule form was prepared in accordance with the same procedures as in Example 27, using trivalerin (Sigma) instead of tricaprylin.

Example 34

The docetaxel-containing pharmaceutical composition for oral administration in the soft capsule form was prepared in accordance with the same procedures as in Example 27, using tricaproin (Sigma) instead of tricaprylin.

Example 35

The docetaxel-containing pharmaceutical composition for oral administration in the soft capsule form was prepared in accordance with the same procedures as in Example 27, using triheptanoin (Sigma) instead of tricaprylin.

Example 36

The docetaxel-containing pharmaceutical composition for oral administration in the soft capsule form was prepared in accordance with the same procedures as in Example 27, using trinonanoin (Sigma) instead of tricaprylin.

Example 37

The docetaxel-containing pharmaceutical composition for oral administration in the soft capsule form was prepared in accordance with the same procedures as in Example 27, using tricaprin (Sigma) instead of tricaprylin.

Example 38

The docetaxel-containing pharmaceutical composition for oral administration in the soft capsule form was prepared in accordance with the same procedures as in Example 27, using triundecanoin (Sigma) instead of tricaprylin.

Example 39

The docetaxel-containing pharmaceutical composition for oral administration in the soft capsule form was prepared in accordance with the same procedures as in Example 27, using trilaurin (Sigma) instead of tricaprylin.

Example 40

The docetaxel-containing pharmaceutical composition for oral administration in the soft capsule form was prepared in accordance with the same procedures as in Example 27, using tritridecanoin (Sigma) instead of tricaprylin.

Example 41

The docetaxel-containing pharmaceutical composition for oral administration in the soft capsule form was prepared in accordance with the same procedures as in Example 27, using trimyristin (Sigma) instead of tricaprylin.

Example 42

The docetaxel-containing pharmaceutical composition for oral administration in the soft capsule form was prepared in accordance with the same procedures as in Example 27, using tripentadecanoin (Sigma) instead of tricaprylin.

Example 43

The docetaxel-containing pharmaceutical composition for oral administration in the soft capsule form was prepared in accordance with the same procedures as in Example 27, using tripalmitin (Sigma) instead of tricaprylin.

Example 44

The docetaxel-containing pharmaceutical composition for oral administration in the soft capsule form was prepared in accordance with the same procedures as in Example 27, using glyceryl triheptadecanoate (Sigma) instead of tricaprylin.

Example 45

The docetaxel-containing pharmaceutical composition for oral administration in the soft capsule form was prepared in accordance with the same procedures as in Example 27, using triolein (Sigma) instead of tricaprylin.

Example 46

The docetaxel-containing pharmaceutical composition for oral administration in the soft capsule form was prepared in accordance with the same procedures as in Example 27, using Capmul™ GMO-50 EP/NF (Abitec) instead of PECEOL™.

Example 47

The docetaxel-containing pharmaceutical composition for oral administration in the soft capsule form was prepared in accordance with the same procedures as in Example 27, using methylene chloride instead of anhydrous ethanol.

Example 48. Paclitaxel-Containing Soft Capsules

Figure 4:
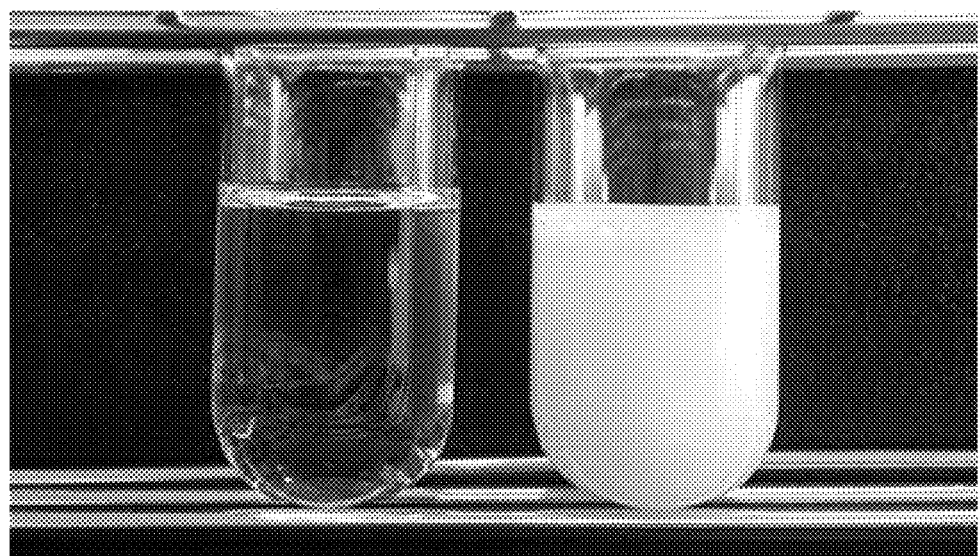
FIG. 4 represents the appearances of the paclitaxel-containing lipid solution prepared in Example 48 and Comparative Example 3. A: the paclitaxel-containing lipid solution prepared in Example 48, B: the paclitaxel-containing lipid solution prepared in Comparative Example 3.

The paclitaxel-containing pharmaceutical composition for oral administration was prepared according to the components and amounts shown in Table 4. Paclitaxel and LABRASOL™ (Gattefosse) were completely dissolved in methylene chloride (about 14 times of the volume of tricaprylin). The resulting solution was dried under reduced pressure at 40° C. to remove methylene chloride. To the resulting mixture, were added tricaprylin (Captex™ 8000, ABITEC), PECEOL™ (Gattefosse), and Tween™ 80. The resulting mixture was stirred at 40° C. to obtain the clear oily solution. The resulting clear oily solution was filled into a soft capsule. The appearance of the clear oily solution is shown in FIG. 4 (left, A).

TABLE 4

| L/I | Component | Amount/ 1 capsule | Ratio (% by weight) |
| --- | --- | --- | --- |
| 1 Taxane | Paclitaxel | 50 mg | 4.84 |
| 2 Medium chain triglyceride | Tricaprylin | 0.14 ml | 12.77 |
| 3 Oleoyl glycerol complex | PECEOL ™ | 0.56 ml | 50.65 |
| 4 Surfactant | Tween ™ 80 | 0.16 ml | 17.42 |
| 5 Polyoxyl glyceryl fatty acid ester | LABRASOL ™ | 0.14 ml | 14.32 |
| | Total | | 100.00 |

Example 49

The paclitaxel-containing pharmaceutical composition for oral administration in the soft capsule form was prepared in accordance with the same procedures as in Example 48, using Gelucire™ 44/14 (Gettafosse) instead of LABRASOL™.

Example 50

The paclitaxel-containing pharmaceutical composition for oral administration in the soft capsule form was prepared in accordance with the same procedures as in Example 48, using Gelucire™ 50/13 (Gettafosse) instead of LABRASOL™.

Example 51

The paclitaxel-containing pharmaceutical composition for oral administration in the soft capsule form was prepared in accordance with the same procedures as in Example 48, using Capmul™ GMO-50 EP/NF (Abitec) instead of PECEOL™.

Example 52

The paclitaxel-containing pharmaceutical composition for oral administration in the soft capsule form was prepared in accordance with the same procedures as in Example 48, using anhydrous ethanol instead of methylene chloride.

Example 53

The paclitaxel-containing pharmaceutical composition for oral administration in the soft capsule form was prepared in accordance with the same procedures as in Example 48, using triacetin (Sigma) instead of tricaprylin.

Example 54

The paclitaxel-containing pharmaceutical composition for oral administration in the soft capsule form was prepared in accordance with the same procedures as in Example 48, using tripropionin (Sigma) instead of tricaprylin.

Example 55

The paclitaxel-containing pharmaceutical composition for oral administration in the soft capsule form was prepared in accordance with the same procedures as in Example 48, using tributyrin (Sigma) instead of tricaprylin.

Example 56

The paclitaxel-containing pharmaceutical composition for oral administration in the soft capsule form was prepared in accordance with the same procedures as in Example 48, using trivalerin (Sigma) instead of tricaprylin.

Example 57

The paclitaxel-containing pharmaceutical composition for oral administration in the soft capsule form was prepared in accordance with the same procedures as in Example 48, using tricaproin (Sigma) instead of tricaprylin.

Example 58

The paclitaxel-containing pharmaceutical composition for oral administration in the soft capsule form was prepared in accordance with the same procedures as in Example 48, using triheptanoin (Sigma) instead of tricaprylin.

Example 59

The paclitaxel-containing pharmaceutical composition for oral administration in the soft capsule form was prepared in accordance with the same procedures as in Example 48, using trinonanoin (Sigma) instead of tricaprylin.

Example 60

The paclitaxel-containing pharmaceutical composition for oral administration in the soft capsule form was prepared in accordance with the same procedures as in Example 48, using tricaprin (Sigma) instead of tricaprylin.

Example 61

The paclitaxel-containing pharmaceutical composition for oral administration in the soft capsule form was prepared in accordance with the same procedures as in Example 48, using triundecanoin (Sigma) instead of tricaprylin.

Example 62

The paclitaxel-containing pharmaceutical composition for oral administration in the soft capsule form was prepared in accordance with the same procedures as in Example 48, using trilaurin (Sigma) instead of tricaprylin.

Example 63

The paclitaxel-containing pharmaceutical composition for oral administration in the soft capsule form was prepared in accordance with the same procedures as in Example 48, using tritridecanoin (Sigma) instead of tricaprylin.

Example 64

The paclitaxel-containing pharmaceutical composition for oral administration in the soft capsule form was prepared in accordance with the same procedures as in Example 48, using trimyristin (Sigma) instead of tricaprylin.

Example 65

The paclitaxel-containing pharmaceutical composition for oral administration in the soft capsule form was prepared in accordance with the same procedures as in Example 48, using tripentadecanoin (Sigma) instead of tricaprylin.

Example 66

The paclitaxel-containing pharmaceutical composition for oral administration in the soft capsule form was prepared in accordance with the same procedures as in Example 48, using tripalmitin (Sigma) instead of tricaprylin.

Example 67

The paclitaxel-containing pharmaceutical composition for oral administration in the soft capsule form was prepared in accordance with the same procedures as in Example 48, using glyceryl triheptadecanoate (Sigma) instead of tricaprylin.

Example 68

The paclitaxel-containing pharmaceutical composition for oral administration in the soft capsule form was prepared in accordance with the same procedures as in Example 48, using triolein (Sigma) instead of tricaprylin.

Example 69. Paclitaxel-Containing Pharmaceutical Composition for Oral Administration The paclitaxel-containing pharmaceutical composition for oral administration was prepared according to the components and amounts shown in Table 5. Paclitaxel and LABRASOL™ (Gattefosse) were completely dissolved in methylene chloride (about 14 times of the volume of tricaprylin). The resulting solution was dried under reduced pressure at 40° C. to remove methylene chloride. To the resulting mixture, were added tricaprylin (Captex™ 8000, ABITEC), PECEOL™ (Gattefosse), and Tween™ 80. The resulting mixture was stirred at 40° C. to obtain the clear oily solution. The resulting clear oily solution was filled into a soft capsule.

TABLE 5

| L/I | Component | Amount/ 1 capsule | Ratio (% by weight) |
| --- | --- | --- | --- |
| 1 Taxane | Paclitaxel | 250 mg | 20.55 |
| 2 Medium chain triglyceride | Tricaprylin | 0.14 ml | 10.11 |
| 3 Oleoyl glycerol complex | PECEOL ™ | 0.56 ml | 43.72 |
| 4 Surfactant | Tween ™ 80 | 0.16 ml | 14.05 |
| 5 Polyoxyl glyceryl fatty acid ester | LABRASOL ™ | 0.14 ml | 11.57 |
| Total | | | 100.00 |

Comparative Example 2

The docetaxel-containing composition was prepared according to the components and amounts shown in Table 6. Docetaxel and tricaprylin (Captex™ 8000, ABITEC) were completely dissolved in ethanol (about 14 times of the volume of tricaprylin). The resulting solution was dried under reduced pressure at 40° C. to remove ethanol. To the resulting mixture, were added PECEOL™ (Gattefosse) and Tween™ 80. The resulting mixture was stirred at 40° C. to obtain the oily solution. The resulting oily solution was an opaque dispersion having white precipitates. The appearance thereof is shown in FIG. 3 (right, B).

TABLE 6

| L/I | Component | Amount/ 1 capsule | Ratio (% by weight) |
| --- | --- | --- | --- |
| 1 Taxane | Docetaxel | 30 mg | 3.01 |
| 2 Medium chain triglyceride | Tricaprylin | 0.28 ml | 26.30 |
| 3 Oleoyl glycerol complex | PECEOL ™ | 0.55 ml | 52.49 |
| 4 Surfactant | Tween ™ 80 | 0.16 ml | 18.20 |
| Total | | | 100.00 |

Comparative Example 3

The paclitaxel-containing composition was prepared according to the components and amounts shown in Table 7. Paclitaxel and tricaprylin (Captex™ 8000, ABITEC) were completely dissolved in methylene chloride (about 14 times of the volume of tricaprylin). The resulting solution was dried under reduced pressure at 40° C. to remove methylene chloride. To the resulting mixture, were added PECEOL™ (Gattefosse) and Tween™ 80. The resulting mixture was stirred at 40° C. to obtain the oily solution. The resulting oily solution was an opaque dispersion having white precipitates. The appearance thereof is shown in FIG. 4 (right, B).

TABLE 7

| L/I | Component | Amount/ 1 capsule | Ratio (% by weight) |
| --- | --- | --- | --- |
| 1 Taxane | Paclitaxel | 30 mg | 3.01 |
| 2 Medium chain triglyceride | Tricaprylin | 0.28 ml | 26.30 |
| 3 Oleoyl glycerol complex | PECEOL ™ | 0.55 ml | 52.49 |
| 4 Surfactant | Tween ™ 80 | 0.16 ml | 18.20 |
| Total | | | 100.00 |

Experimental Example 3. Stability Evaluation of Gelatin Capsules

The soft capsules prepared in Example 27 and Example 48 were placed in a HDPE bottle, which was then stored under the conditions of 25° C. and 60% (RH) for 6 months to evaluate the stability of the gelatin capsules. Stability of the gelatin capsules was evaluated through observing the appearances thereof and a leak therefrom. The results are shown in the following Table 8.

TABLE 8

|  |  | Example 27 | Example 48 |
|---|---|---|---|
| 1 month | Leak | No leak occurred | No leak occurred |
|  | Appearance | No appearance changed | No appearance changed |
| 3 months | Leak | No leak occurred | No leak occurred |
|  | Appearance | No appearance changed | No appearance changed |
| 6 months | Leak | No leak occurred | No leak occurred |
|  | Appearance | No appearance changed | No appearance changed |

From the results of Table 8, it can be seen that the soft capsules prepared according to the present invention have excellent stability.

Experimental Example 4. Evaluation of In Vivo Absorption Rate

The docetaxel-containing oily solution prepared in Example 27 was orally administered in the dose of 125 mg/kg to ICR mice (6 week old, female, Orient Bio, Republic of Korea), using a gastric zonde. At 0 minute, 15 minutes, 30 minutes, 1 hour, 2 hours, 4 hours, and 6 hours after the drug administration, the blood samples were taken from the orbital veins of the mice and then centrifuged at 8,000×g at 4° C. for 20 minutes to obtain the plasma samples, which were stored at −70° C.

The plasma samples were melted at room temperature and then stirred with a vortex mixer for 1 minute. The internal standard solution (paclitaxel 10 μg/mL, in acetonitrile) (200.0 μL) and acetonitrile (400.0 μL) were added to the plasma samples (200.0 μL), which were then stirred with a vortex mixer at 3,000 rpm for 5 minutes. Each of the samples were centrifuged at 14,000×g under the condition of 8° C. for 20 minutes. Each supernatant (300 μL) was taken therefrom and then filtered through syringe filter (PTFE, chromdisc, 13 mm, pore size 0.20 mm). The filtrate (200.0 μL) was taken therefrom and then subject to the HPLC analysis.

The conditions for HPLC analysis are as follows.
HPLC: Shimadzu LC-20AD
Detector: Shimadzu SPD-20A
Column: Shim-pack GIS, 5 μm ODS, 250×4.6 mm id.
Data processor: Labsolutions, Shimadzu
Injection volume: 100.0 μL
Flow rate: 1.0 mL/min
Column temperature: 40° C.
Detection wave length: 227 nm
Mobile phase: (A) ACN, (B) DW (ACN: acetonitrile, DW: distilled water)

| Time (minute) | Mobile phase (A) | Mobile phase (B) |
|---|---|---|
| 0 | 30 | 70 |
| 30 | 60 | 40 |
| 35 | 100 | 0 |
| 40 | 0 | 100 |
| 45 | 30 | 70 |

The pharmacokinetic parameters calculated from the blood concentrations of docetaxel measured in the above are shown in Table 9.

TABLE 9

| Cmax (μg/mL) | 6.162 |
|---|---|
| Tmax (hr) | 0.25 |
| $AUC_{0-6\ hr}$ (μg · hr/mL) | 5.635 |
| $AUC_{0-\infty}$ (μg · hr/mL) | 5.928 |

From the results of Table 9, it can be seen that the pharmaceutical composition according to the present invention was rapidly absorbed from the beginning and exhibited remarkably increased in vivo absorption rate.

Experimental Example 5. Evaluation of In Vivo Absorption Rate

The paclitaxel-containing oily solution prepared in Example 48 was orally administered in the dose of 250 mg/kg to ICR mice (6 week old, female, Orient Bio, Republic of Korea), using a gastric zonde. At 0 minute, 15 minutes, 30 minutes, 1 hour, 2 hours, 4 hours, and 6 hours after the drug administration, the blood samples were taken from the orbital veins of the mice and then centrifuged at 8,000×g at 4° C. for 20 minutes to obtain the plasma samples, which were stored at −70° C.

The plasma samples were melted at room temperature and then stirred with a vortex mixer for 1 minute. The internal standard solution (docetaxel 10 μg/mL, in acetonitrile) (200.0 μL) and acetonitrile (400.0 μL) were added to the plasma samples (200.0 μL), which were then stirred with a vortex mixer at 3,000 rpm for 5 minutes. Each of the samples were centrifuged at 14,000×g under the condition of 8° C. for 20 minutes. Each supernatant (300 μL) was taken therefrom and then filtered through syringe filter (PTFE, chromdisc, 13 mm, pore size 0.20 mm). The filtrate (200.0 μL) was taken therefrom and then subject to the HPLC analysis, under the same conditions for HPLC analysis as in Experimental Example 1.

The pharmacokinetic parameters calculated from the blood concentrations of paclitaxel measured in the above are shown in Table 10.

TABLE 10

| Cmax (μg/mL) | 4.207 |
|---|---|
| Tmax (hr) | 0.5 |
| $AUC_{0-6\ hr}$ (μg · hr/mL) | 7.698 |
| $AUC_{0-\infty}$ (μg · hr/mL) | 7.800 |

From the results of Table 10, it can be seen that the pharmaceutical composition according to the present invention was rapidly absorbed from the beginning and exhibited remarkably increased in vivo absorption rate.

The invention claimed is:

1. A pharmaceutical composition for oral administration, consisting essentially of:
   (a) 0.8 to 1.2% by weight of paclitaxel or docetaxel,
   (b) 25 to 30% by weight of a medium chain triglyceride,
   (c) 50 to 55% by weight of an oleoyl glycerol complex having 30 to 65% by weight of monooleoyl glycerol contents; 15 to 50% by weight of dioleoyl glycerol contents; and 2 to 20% by weight of trioleoyl glycerol contents, and
   (d) 15 to 20% by weight of a surfactant selected from the group consisting of polyoxyethylene-polyoxypropylene block copolymer, sorbitan ester, polyoxyethylene sorbitan, and polyoxyethylene ether,
   wherein the pharmaceutical composition is in a clear solution form at room temperature, and wherein the pharmaceutical composition is changed to a clear solution form when it is allowed to stand at room temperature after being stored at 4° C.

2. The pharmaceutical composition for oral administration according to claim 1, wherein the oleoyl glycerol complex has 32 to 52% by weight of monooleoyl glycerol contents; 30 to 50% by weight of dioleoyl glycerol contents; and 5 to 20% by weight of trioleoyl glycerol contents.

3. The pharmaceutical composition for oral administration according to claim 1, wherein the oleoyl glycerol complex has 55 to 65% by weight of monooleoyl glycerol contents; 15 to 35% by weight of dioleoyl glycerol contents; and 2 to 10% by weight of trioleoyl glycerol contents.

4. The pharmaceutical composition for oral administration according to claim 1, wherein the medium chain triglyceride is one or more selected from the group consisting of triacetin, tripropionin, tributyrin, trivalerin, tricaproin, tricaprylin, tricaprin, triheptanoin, trinonanoin, triundecanoin, trilaurin, tritridecanoin, trimyristin, tripentadecanoin, tripalmitin, glyceryl triheptadecanoate, and triolein.

* * * * *